United States Patent
Kracke et al.

(10) Patent No.: US 9,217,002 B2
(45) Date of Patent: Dec. 22, 2015

US009217002B2

(54) CLUSTER BORON COMPOUNDS AND USES THEREOF

(75) Inventors: George R. Kracke, Columbia, MO (US); Yulia Sevryugina, Columbia, MO (US); Marion Frederick Hawthorne, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

(21) Appl. No.: 14/345,042

(22) PCT Filed: Sep. 13, 2012

(86) PCT No.: PCT/US2012/055181
§ 371 (c)(1),
(2), (4) Date: Oct. 15, 2014

(87) PCT Pub. No.: WO2013/040222
PCT Pub. Date: Mar. 21, 2013

(65) Prior Publication Data
US 2015/0072956 A1    Mar. 12, 2015

Related U.S. Application Data

(60) Provisional application No. 61/573,989, filed on Sep. 15, 2011.

(51) Int. Cl.
*C07F 5/02* (2006.01)
*C07F 5/05* (2006.01)

(52) U.S. Cl.
CPC .. *C07F 5/027* (2013.01); *C07F 5/05* (2013.01)

(58) Field of Classification Search
CPC ...................................................... C07F 5/027
USPC ............................................ 514/64; 564/8, 9
See application file for complete search history.

(56) References Cited

U.S. PATENT DOCUMENTS

| 6,392,068 B1 | 5/2002 | Lu et al. |
| 6,664,426 B1 | 12/2003 | Hawthorne et al. |
| 7,842,278 B2 | 11/2010 | Lee et al. |
| 2011/0021735 A1* | 1/2011 | Liu et al. ........................ 528/7 |

FOREIGN PATENT DOCUMENTS

| WO | 2008/145733 A2 | 12/2008 |
| WO | 2013/040222 A1 | 3/2013 |

OTHER PUBLICATIONS

Waxman et al Proc. Natl. Acad. Sci. USA vol. 96, pp. 7635-7639, Jul. 1999.*
Li and Xiong Int. J. Physiol. Pharmacol. 2011, 3(2), 156-166.*
Dong, K. Invert Neurosci. Mar. 2007 7(1), 17-30.*
Lisovskii et al Zhurnal Neorganicheskoi Khimii 2005, 50, 24-32.*
Borkovek et al Journal of Economic Entomology 1969, 62(6) 14-72-1480.*
Costa; Synthesis and antispasmodic activity of lidocaine derivatives endowed with reduced local anesthetic action; ScienceDirect Bioorganic & Medicinal Chemistry Letters, vol. 18 (2008); pp. 1162-1166.
Eriksson; Palladium-catalyzed cross-coupling reactions of arylboronic acids and 2-l-p-carborane; Journal of Organometallic Chemistry, vol. 657 (2002); pp. 267-272.
Grimes; Properties of o-carboranyl carboxylic acids; 2nd Edition (2011); pp. 425-638.
International Bureau of WIPO; International search report and written opinion; Nov. 20, 2012.
Issa; Boron in Drug Discovery: Carboranes as Unique Pharmacophores in Biologically Active Compounds; Chemical Reviews vol. 111 (2011); pp. 5701-5722.
Jiang; Iodination Reactions of Icosahedral para-Carborane and the Synthesis of Carborane Derivatives with Boron—Carbon Bonds; Inorganic Chemistry, vol. 34, No. 13 (1995); pp. 3491-3498.
Li; Simple Syntheses and Alkylation Reactions of 3-Iodo-o-carborane and 9,12-Diiodo-o-carborane1; Inorganic Chemistry, vol. 30, No. 25 (1991); pp. 4866-4868.
Scholz; Synthesis and Evaluation of Carbaborane Derivatives of Indomethacin as Cyclooxygenase Inhibitors; Bioorganic & Medicinal Chemistry Letters, vol. 19, No. 10 (2011); pp. 3242-3248.
Sevryugina; Novel Approach to Aminocarboranes by Mild Amidation of Selected Iodo-carboranes; Inorganic Chemistry, vol. 49 (2010); pp. 10627-10634.
Tyagarajan; Substituted biaryl oxazoles, imidazoles, and thiazoles as sodium channel blockers; Bioorganic & Medicinal Chemistry Letters, vol. 20 (2010); pp. 5536-5540.
Valliant; The medicinal chemistry of corboranes; Coordination Chemistry Reviews; vol. 232 (2002); pp. 173-230.
Zakharkin, "Synthesis and neurotropic properties of nitrogen-containing derivatives of ortho-carborane and nidoortho-carborane anion", Khimiko-Farmatsevticheskii Zhurnal, 1976, vol. 10, pp. 57-63.

* cited by examiner

*Primary Examiner* — David K O Dell
(74) *Attorney, Agent, or Firm* — Polsinelli PC

(57) ABSTRACT

The present invention relates to novel cluster boron compounds and their use as sodium channel blockers. In particular, the novel cluster boron compounds may be lidocaine analogs where the aromatic ring of the lidocaine molecule is replaced with a cluster boron group. The invention also provides methods for making the cluster boron compounds comprising contacting a halogenated cluster boron with an amino acetamide in the presence of a catalyst, a proton acceptor, and a ligand.

12 Claims, 7 Drawing Sheets

CLUSTER BORON COMPOUNDS AND USES THEREOF

CROSS-REFERENCE TO RELATED APPLICATIONS

This application claims priority to U.S. Provisional Application No. 61/573,989 filed Sep. 15, 2011, which is hereby incorporated by reference in its entirety.

FIELD

The present invention relates to novel cluster boron compounds and their use as sodium channel blockers. The invention also provides methods for making and using the compounds.

BACKGROUND

The sodium channel is an integral part of nerve and cardiac cell conduction pathways and has been an important drug target for many pharmaceuticals, such as analgesics, antiarrhythmic, anticonvulsants, and antidepressants. Disruption of these pathways by sodium channel blockers provides the basis for their therapeutic actions.

The concept of cluster borons as pharmacophores in biologically active molecules is a developing area of research. In fact, incorporation of any boron containing moiety in drug design has only recently been explored.

Some cluster boron structures have been shown to exhibit a diverse set of biological activities. In particular, through their unique properties, they are thought to be capable of providing selectivity. In particular, selectivity among sodium channel receptor subtypes is important in increasing the effectiveness of treatments and at the same time reducing side effects.

Therefore, there is a need to provide new molecule sodium channel blockers and their syntheses.

SUMMARY

In one aspect, the present disclosure provides a compound comprising Formula (I):

Formula (I)

wherein
B is a cluster boron;
$R^1$ is hydrocarbyl or substituted hydrocarbyl;
$R^2$ and $R^3$ are independently chosen from hydrogen, hydrocarbyl, and substituted hydrocarbyl;
and $R^1$, $R^2$, and $R^3$ may form one or more rings.

In another aspect, the disclosure provides a compound comprising Formula (II):

Formula (II)

wherein
B is a cluster boron;
$R^1$ represents hydrocarbyl or substituted hydrocarbyl;
$R^2$ and $R^3$ are independently chosen from hydrogen, hydrocarbyl, and substituted hydrocarbyl;
and $R^1$, $R^2$, and $R^3$ may form one or more rings.

In still another embodiment, the disclosure provides a compound comprising Formula (III):

Formula (III)

wherein
B is a cluster boron;
and $R^1$ represents hydrocarbyl or substituted hydrocarbyl; and
$R^2$ and $R^3$ represent hydrogen, hydrocarbyl, or substituted hydrocarbyl;
$R^1$, $R^2$, and $R^3$ may form one or more rings.

In other aspects, the disclosure provides a compound of Formula (I), (II), or (III) and a pharmaceutically acceptable excipient.

In yet another aspect, the disclosure provides a method for forming a compound comprising Formula (I), the method comprising contacting a halogenated cluster boron with an amino acetamide in the presence of a catalyst, a phosphate, and a ligand to form the compound comprising Formula (I):

Formula (I)

wherein
B is a cluster boron;
$R^1$ represents hydrocarbyl or substituted hydrocarbyl;
$R^2$ and $R^3$ are independently chosen from hydrogen, hydrocarbyl, and substituted hydrocarbyl;
and $R^1$, $R^2$, and $R^3$ may form one or more rings.

In still a further aspect, the disclosure provides a method of treating a condition associated with sodium channel function in a subject, the method comprising administering to the subject a cluster boron substituted lidocaine or a cluster boron substituted lidocaine derivative.

Other features and iterations of the disclosure are described in more detail herein.

DESCRIPTION OF THE FIGURES

FIGS. 4(a) to 4(d) show inhibition of voltage gated sodium channels.

FIGS. 5(a) to 5(d) show analgesia when injected into the hind limb of mice in hot plate experiments.

DETAILED DESCRIPTION OF INVENTION

Briefly, therefore, the present invention relates to novel cluster boron compounds. In particular, the novel cluster boron compounds may be lidocaine analogs where the aromatic ring of the lidocaine molecule is replaced with a cluster boron group. The cluster boron functionality is unique in that, unlike a phenyl group, it may result in fewer pi-pi interactions with the target site. Further, boron is thought to be metabolized more slowly than other groups because of the foreign nature of boron in biological structures. Finally, unique substitutions of the icosahedral binding allow tunability of the molecule's properties and may improve selectivity of the compounds.

(I). Compounds
  a. Compound Comprising Formula (I)
  In one aspect, a compound comprising Formula (I) is provided:

Formula (I)

wherein
B is a cluster boron;
$R^1$ is hydrocarbyl or substituted hydrocarbyl;
$R^2$ and $R^3$ are independently chosen from hydrogen, hydrocarbyl, and substituted hydrocarbyl;
and $R^1$, $R^2$ and $R^3$ may form one or more rings.

B in the compound comprising Formula (I) represents a cluster boron compound. Cluster boron may be either an icosahedral boron or a nido boron compound.

For an icosahedral boron, the compound contains twelve vertexes which may be boron or carbon atoms. In some aspects, all vertices are boron atoms. As will be understood in the art, the valence of boron is such that the boron atoms making up the icosahedral structure may be bonded to a further substituent. The cluster may be closo. Exemplary icosahedral compounds include closo carboranes. Thus, the boron atoms may be bonded to one or more substituents, by way of non-limiting example, hydrogen, hydrocarbyl, substituted hydrocarbyl, amino, amido, azo, esters, ethers, halogens, hydroxy, nitro, mercapto, phosphino, or sulfonated groups. In other embodiments, the icosahedral boron compound comprises one or more carbons in the icosahedral structure. Similarly, the carbon atoms comprising the icosahedral structure may be bonded to one or more additional substituents, these may be chosen from, for example, hydrogen, hydrocarbyl, substituted hydrocarbyl, amino, amido, azo, esters, ethers, halogens, hydroxy, nitro, mercapto, phosphino, or sulfonated groups.

The boron cluster may be a nido compound. The nido compound has 11 vertexes. The nido compound may be substituted, by way of non-limiting example, hydrogen, hydrocarbyl, substituted hydrocarbyl, amino, amido, azo, esters, ethers, halogens, hydroxy, nitro, mercapto, phosphino, or sulfonated groups similarly to the icosahedral compounds. Exemplary nido compounds include 7,8-, 7,9- and 2,9-$C_2B_9H_{12}^-$ which is substituted with the remainder of the compound comprising Formula (I).

The incorporation of carbon into the icosahedral or nido structure may occur at any vertex. For example, the cluster boron may contain 1, 2, 3, 4, 5, 6, 7, 8, 9, 10, or 11 carbon atoms in a twelve vertex compound, and 1, 2, 3, 4, 5, 6, 7, 8, 9, or 10 borons in an 11 vertex compound. Due to the three dimensional nature of the cluster boron compound, addition of more than one carbon in the cluster boron structure may create different structural isomers. For example, where two carbon atoms are present in the icosahedral structure the two carbon atoms may produce configurations described as ortho, meta, and para. In some preferred embodiments, the cluster boron is a carborane having two carbon atoms, wherein the carbon atoms are configured ortho to each other ([1,2-$C_2B_{10}$]), meta to each other ([1,7-$C_2B_{10}$]), or para ([1,12-$C_2B_{10}$]) to each other. When more than two carbon atoms are in the cluster boron, they can similarly be set in the cluster at any position without limitation.

The cluster boron is bound to the remainder of the compound comprising Formula (I) through an amide linkage at one of the vertexes of the icosahedral structure. Linkage can occur at any point on the icosahedral structure. In some embodiments, the cluster boron is linked to the amide of the compound comprising Formula (I) through a boron atom vertex. In other embodiments, the cluster boron is linked to the amide of the compound comprising Formula (I) through a carbon atom vertex. In preferred embodiments, the linkage occurs through boron atom vertexes: 2-in para-carborane, 3-in ortho-carborane and 9-in meta-carborane.

$R^1$ represents hydrocarbyl or substituted hydrocarbyl. In some embodiments, $R^1$ is hydrocarbyl chosen from alkyl and alkenyl. $R^1$ may be branched, straight chain, or may form a ring with $R^2$ or $R^3$. In one embodiment, $R^1$ comprises 1 to 10 atoms. In other embodiments, $R^1$ comprises from 1 to 6 atoms. The linear portion of the chain may comprise 1, 2, or 3 carbon atoms which may be substituted, preferably with hydrogen or alkyl groups. In some embodiments $R^1$ is chosen from —$CH_2$—, —$CH(CH_3)$—, —$C(CH_3)_2$—, —$CH_2CH_2$—, —$CH_2CH(CH_3)$—, and —$CH(CH_2CH_3)$—.

$R^2$ and $R^3$ can and will vary within the formula. $R^2$ and $R^3$ may be independently selected from hydrogen, hydrocarbyl, and substituted hydrocarbyl. $R^2$ and $R^3$ may be, in some embodiments, hydrocarbyl. In one embodiment, $R^2$ and $R^3$ comprise 1 to 10 atoms. In other embodiments, $R^2$ and $R^3$ comprise from 1 to 6 atoms. In preferred embodiments, $R^2$ and $R^3$ comprise a saturated linear, branched, or cyclic hydrocarbon chain. In particularly preferred embodiments, $R^2$ and $R^3$ are independently chosen from methyl, ethyl, propyl, isopropyl, butyl, sec-butyl, isobutyl, tert-butyl, pentyl, hexyl, heptyl and the like.

$R^2$ and $R^3$ may also be linked to form a ring. In some embodiments, the ring can comprise 1 to 10 atoms. In other embodiments, the ring comprises from 1 to 6 atoms. In preferred embodiments, the ring is a saturated hydrocarbon five, six, seven or eight membered ring. The ring may be linear or branched. In embodiments where the ring is branched, the branching may be selected from hydrogen or hydrocarbyl, and is most preferably lower alkyl, including but not limited to methyl, ethyl, propyl, isopropyl, butyl, sec-butyl, isobutyl, tert-butyl, pentyl, hexyl, heptyl and the like.

In some embodiments, $R^1$ and $R^2$ or $R^1$ and $R^3$ form a ring. The ring may comprise 1 to 15 atoms and may be monocyclic, bicyclic, or have multiple cyclic structures. In some embodiments, the ring is chosen from a five member ring, a six member ring, or a seven member ring. The ring may be carbocyclic or heterocyclic. In some aspects, $R^1$ and $R^2$ or $R^3$ are bonded to form a —$CH_2CH_2$— moiety, in other aspects, $R^1$ and $R^2$ or $R^3$ are bonded to form a —$CH_2CH_2CH_2$— moiety. Where $R^1$ is bonded to $R^2$, $R^3$ may be chosen from hydrogen, hydrocarbyl and substituted hydrocarbyl. Similarly, where $R^1$ is bonded to $R^3$, $R^2$ may be chosen from hydrogen, hydrocarbyl, and substituted hydrocarbyl.

Exemplary compounds of the compound comprising Formula (I) are given in TABLE 1.

TABLE 1

Exemplary Compounds Comprising Formula (I)

TABLE 1-continued

Exemplary Compounds Comprising Formula (I)

Figure 1:
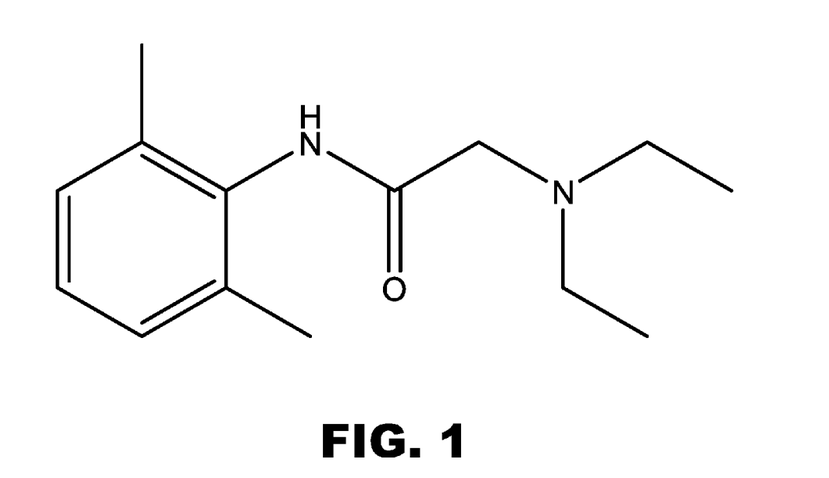
FIG. 1 is the chemical structure of lidocaine.
Figure 2:
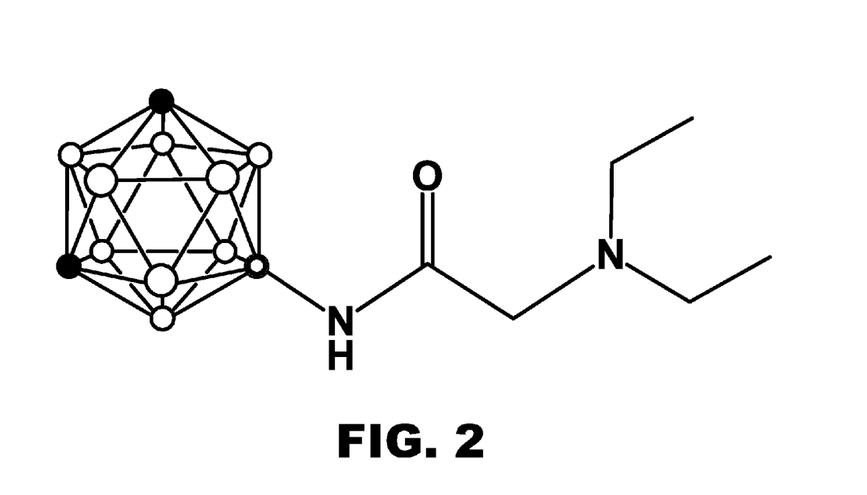
FIG. 2 is general molecular structure of the m-carborane lidocaine.
Figure 3:
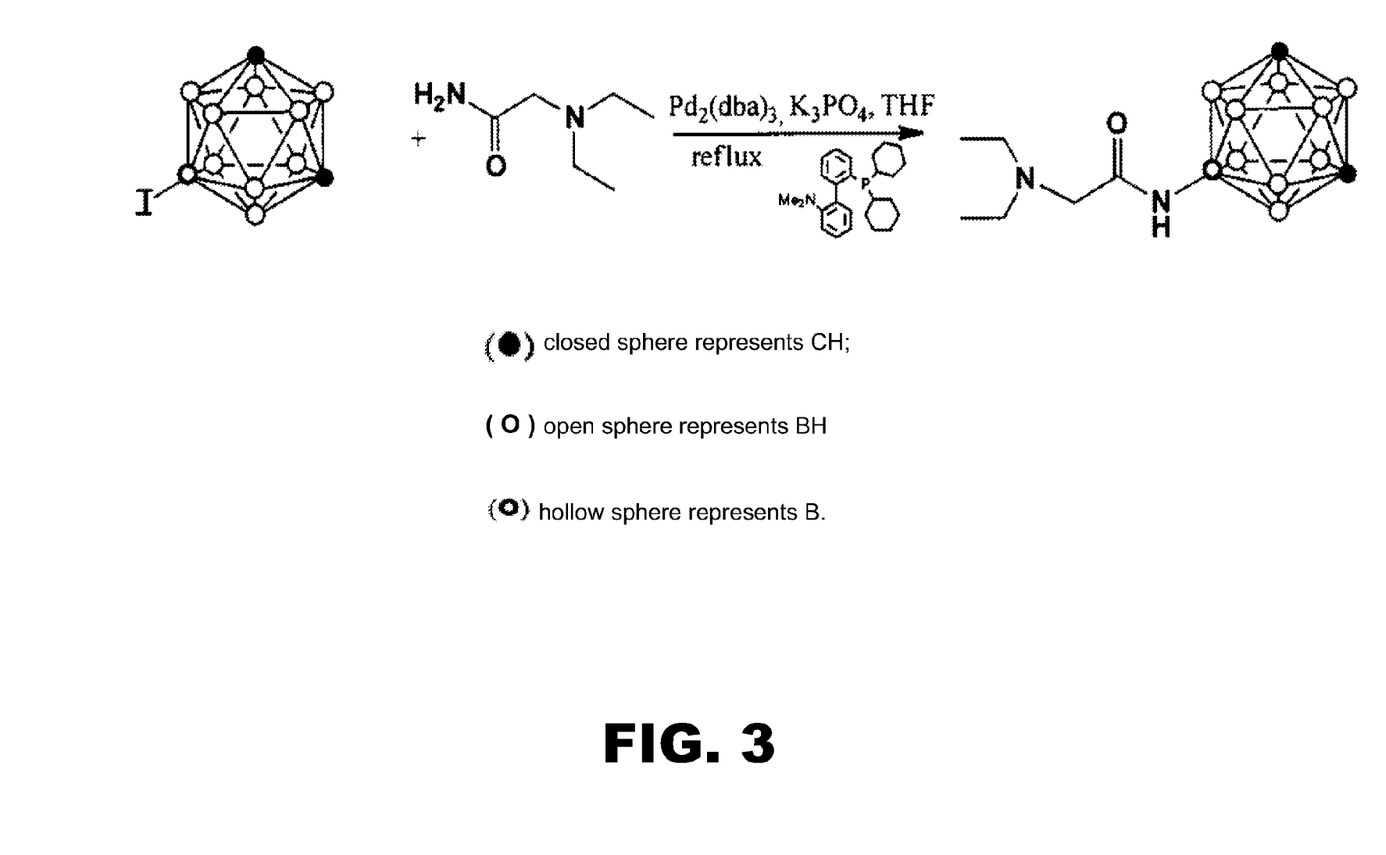
FIG. 3 is an exemplary synthetic scheme for the m-carborane substituted lidocaine, according to one embodiment of the invention.
Figure 4:
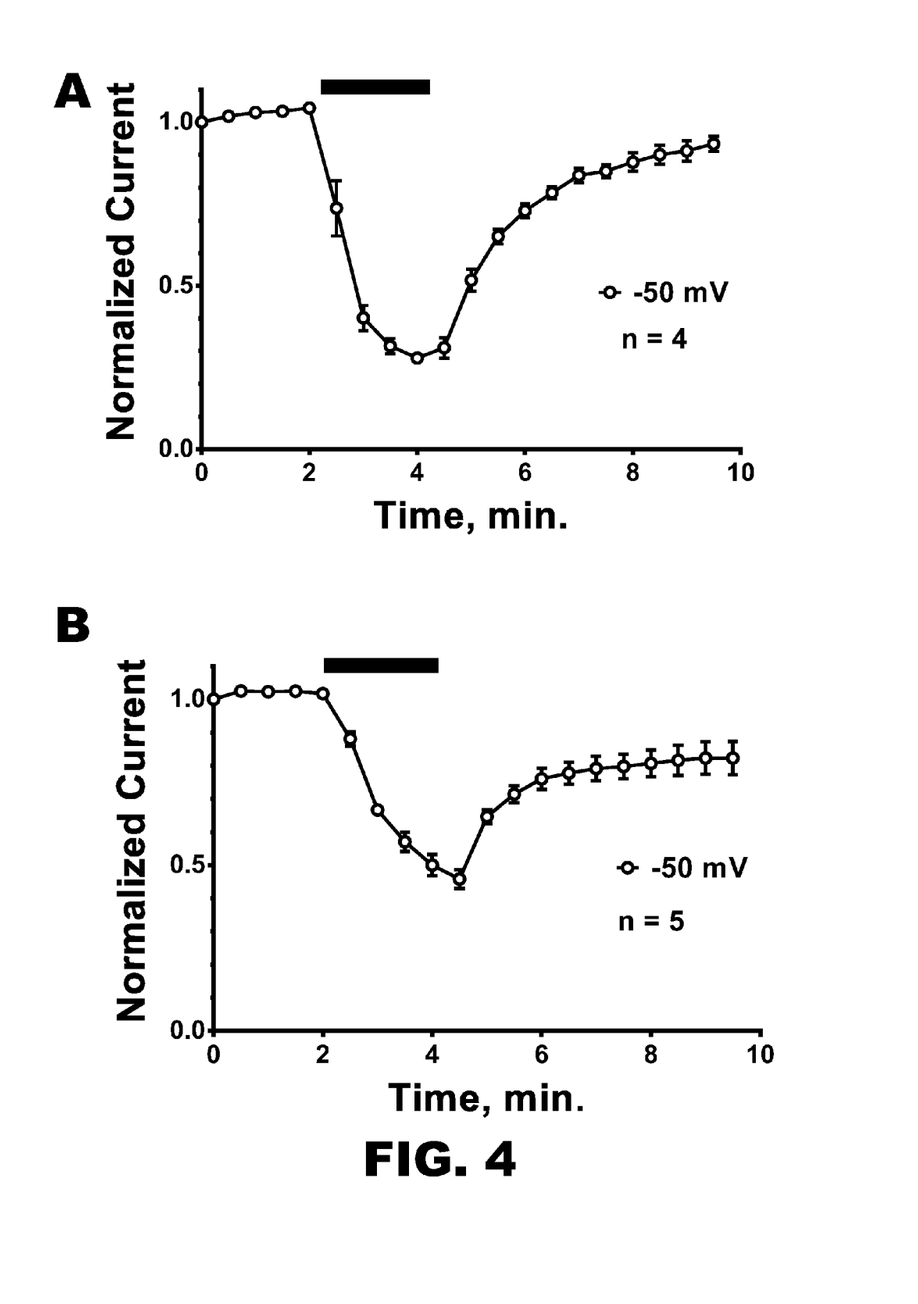
FIG. 4(a) shows lidocaine.
FIG. 4(b) shows o-carborane lidocaine.
FIG. 4(c) shows m-carborane lidocaine.
FIG. 4(d) shows p-carborane lidocaine.
Figure 5:
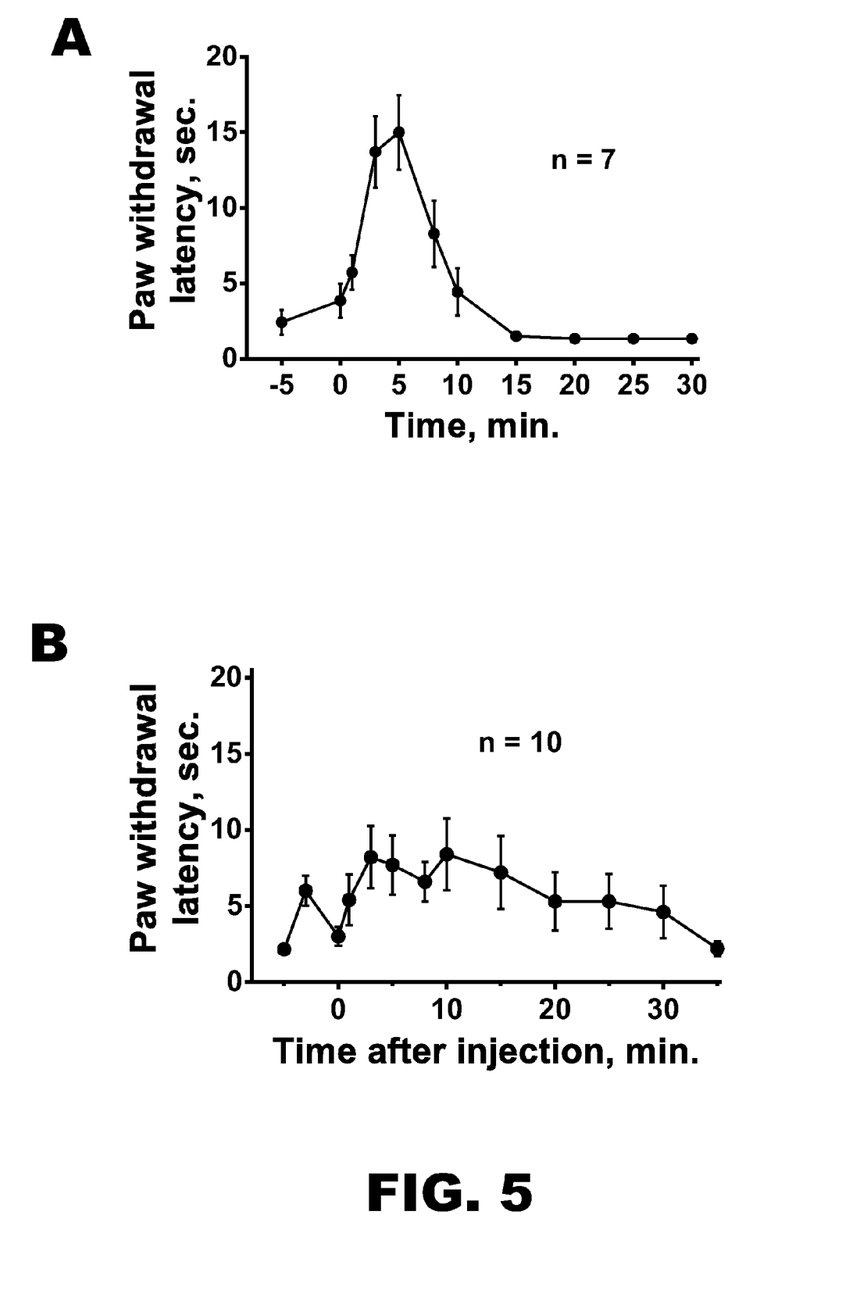
FIG. 5(a) shows lidocaine.
FIG. 5(b) shows o-carborane lidocaine.
FIG. 5(c) shows m-carborane lidocaine.
FIG. 5(d) shows p-carborane lidocaine.

In the above figures and herein closed sphere represents CH; open sphere represents BH, and hollow sphere represents B atom. FIG. 3 also provides a graphic of these representations.

b. Compound Comprising Formula (II)

In another aspect, the disclosure provides for a compound comprising Formula (II):

Formula (II)

wherein

B is a cluster boron;

$R^1$ represents hydrocarbyl or substituted hydrocarbyl;

$R^2$ and $R^3$ are independently chosen from hydrogen, hydrocarbyl, and substituted hydrocarbyl;

and $R^1$, $R^2$, and $R^3$ may form one or more rings.

B, $R^1$, $R^2$ and $R^3$ are as described in section (I)(a). Rather than the amide linkage of Formula (I), the compounds of Formula (II) are linked to the cluster boron by an ester. The linkage may occur on any site of the cluster boron as described in section (I)(a). Exemplary compounds comprising Formula (II) are shown in TABLE 2.

TABLE 2

Exemplary Compounds Comprising Formula (II)

c. Compound Comprising Formula (III)

In still another aspect of the present disclosure, a compound comprising Formula (III) is provided:

Formula (III)

wherein
B is a cluster boron;
R¹ represents hydrocarbyl or substituted hydrocarbyl; and
R² and R³ represent hydrogen, hydrocarbyl, or substituted hydrocarbyl;
and R¹, R², and R³ may form one or more rings.

B and R¹, R², and R³ areas described in section (I)(a). In some embodiments, R² and R³ are linked to form an oxygen containing ring. In addition to the oxygen atom, the ring may contain one or more additional heteroatoms. Preferred heteroatoms include nitrogen. The ring may be saturated or unsaturated. Rather than the amide linkage of Formula (I), the compounds of Formula (III) are linked to the cluster boron by an ether. The linkage may occur on any site of the cluster boron as described in section (I)(a).

In one aspect, the composition comprises Formula (III)(a):

wherein B is a cluster boron.

In another aspect, the composition comprises Formula (III)(b):

wherein B is a cluster boron.

In some aspects, the compounds comprising Formulas (I), (II), and (III) will contain chiral centers. Where the formulas contain chiral centers, each chiral center may be selected from (R) and (S). In some embodiments, the compounds comprising Formula (I), (II), and (III) will be isolated in an (R) configuration. In other embodiments, the compounds comprising Formula (I), (II), and (III) will be isolated in an (S) configuration. In some embodiments, the compounds comprising Formula (I), (II), and (III) will be racemic mixtures.

In some embodiments, the compounds comprising Formula (I), (II), and (III) may be used or isolated as salts. Preferably, the salt will be a pharmaceutically acceptable salt. Pharmaceutically acceptable salts include, without limitation, hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpriopionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like.

(II). Pharmaceutical Compositions

In one aspect, the invention provides a pharmaceutical composition comprising the compounds comprising Formula (I), (II), or (III) and at least one pharmaceutically acceptable excipient.

a. Compounds Comprising Formula (I), (II), and (Ill)

The pharmaceutical compositions comprise one of the compounds comprising Formula (I), (II), or (III) as described in section (I).

b. Pharmaceutically Acceptable Excipient

The pharmaceutical compositions comprise at least one pharmaceutically acceptable excipient. Non-limiting examples of suitable excipients include diluents, binders, fillers, buffering agents, pH modifying agents, disintegrants, dispersing agents, stabilizers, preservatives, and coloring agents. The amount and types of excipients may be selected according to known principles of pharmaceutical science.

In one embodiment, the excipient may include at least one diluent. Non-limiting examples of suitable diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose.

In another embodiment, the excipient may comprise a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Representative examples of suitable buffering agents include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be sodium carbonate or sodium bicarbonate.

In another alternate embodiment, the excipient may also include a preservative. Non-limiting examples of suitable preservatives include antioxidants, such as alpha-tocopherol or ascorbate.

In a further embodiment, the excipient may include a disintegrant. Suitable disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In a further embodiment, the excipient may include a lubricant. Non-limiting examples of suitable lubricants include minerals such as talc or silica; and fats such as vegetable stearin, magnesium stearate or stearic acid.

In still another embodiment, it may be desirable to provide a coloring agent. Suitable color additives include, but are not limited to, food, drug and cosmetic colors (FD&C), drug and cosmetic colors (D&C), or external drug and cosmetic colors (Ext. D&C).

The weight fraction of the excipient(s) in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The pharmaceutical composition may be mixed with one or more excipients to form a solid, liquid or cream dosage form.

c. Additional API

Optionally, the compounds comprising Formula (I), (II), or (III) may be combined with each other or may be combined with another active pharmaceutical ingredient. Additional pharmaceutical agents may include, without limitation, antiarrythmics, anticonvulsants, antidepressants, cardiovascular agents, sodium channel blockers, cardiovascular agents, antibiotics and analgesics.

(III). Methods of Making

The compound comprising Formula (I) may be synthesized by reaction of an amino acetamide and a halogenated cluster boron. The reaction is generally catalyzed by addition of a metal catalyst and ligand.

The halogenated cluster boron is as described in section (I)(a) where the cluster boron is halogenated in at least one vertex. Preferably, the halogen is iodine or bromine. Halogenated cluster borons may be prepared, as is understood in the art, using a cluster boron salt such as a lithium salt and reacting with boron trihalide. For example $Li_2[C_2B_9H_{11}]$ may be reacted with boron triiodide in hexane. Exemplary cluster borons include 3-iodo-o-carborane, 9-iodo-m-carborane, and 2-iodo-p-carborane.

The amino acetamide may be synthesized by standard organic chemistry. In general, the amino acetamide is added to the reaction in excess to the halogenated cluster boron. In some embodiments, the mole to mole ratio of the halogenated cluster boron to the amino acetamide can range from about 1:1.1 to about 1:10. In some embodiments, the mole to mole ratio of the cluster boron compound to amino acetamide is about 1:1.5, about 1:2, about 1:2.5, about 1:3, about 1:3.5, about 1:4, about 1:4.5, about 1:25 or higher. In an exemplary embodiment, the mole to mole ratio of the cluster boron compound to amino acetamide is about 1:1.3 to 1:3.

The cluster boron compound is coupled to the amino acetamide using a catalyst and ligand. The catalyst may be selected from metals such as Pt, Pd, Rh, Ir, Ru, Au, Ag, Hg, and Os or mixtures thereof. The catalysts may be coordinated to a preferred oxidation state for example to triphenylphosphine or dibenzylidineacetone (dba). In one preferred embodiment, the catalyst is Pd(0) in the form of $Pd_2(dba)_3$.

The catalyst is generally added in a catalytic amount. In some aspects, the catalyst is provided in amounts ranging from 0.1 mol % to 10 mol % to the halogenated cluster boron reactant. In another embodiment, the catalyst is added in an amount ranging from 0.5 mol % to about 5 mol % the halogenated cluster boron reactant. In various embodiments, the catalyst is added to the reaction in an amount of about 0.5 mol %, about 1 mol %, about 1.5 mol %, about 2 mol %, about 2.5 mol %, about 3.0 mol %, about 3.5 mol %, about 4 mol %, about 4.5 mol %, or about 5 mol % to the halogenated cluster boron compound.

A ligand is also added to facilitate the reaction. The ligand may be selected from mono- , bi- or poly-dentate ligands. Ligands which bind the metal through one or more carbon nitrogen, sulfur or phosphorus atoms or mixtures thereof—e.g., phosphines, organo-phosphorus compounds, amines and heterocyclic organic compounds containing ring nitrogens and/or sulfur atoms may be used. Exemplary ligands include biaryl phosphine ligands, such as 2-biphenyl-di-t-butyl phosphine (JohnPhos), (2-biphenyl)dicyclohexylphosphine, 2-dicyclohexylphosphino-2',4',6'-triisopropylbiphenyl (XPhos), 2-di-t-butylphosphino-2',4',6'-triisopropylbiphenyl (tBuXPhos), 2-di-t-butylphosphino-3,4,5,6-tetramethyl-2',4',6'-triisopropylbiphenyl (Me₄tBuXPhos), 2-{bis[3,5-bis(trifluoromethyl)phenyl]phosphino}-3,6-dimethoxy-2',4',6'-triisopropylbiphenyl (JackiePhos), 2-dicyclohexylphosphino-2',6'-dimethoxy biphenyl (SPhos), 2-(dicyclohexylphosphino)3,6-dimethoxy-2',4',6'-triisopropylbiphenyl (BrettPhos), 2-(di-t-butylphosphino)3,6-dimethoxy-2',4',6'-triisopropylbiphenyl (tBuBrettPhos), 2-dicyclohexylphosphino-2',6'-diisopropoxybiphenyl (RuPhos), 2-dicyclohexylphosphino-2'-(N,N-dimethylamino)biphenyl (DavePhos). In an exemplary embodiment, the ligand is 2-dicyclohexylphosphosphino-2'-(N,N-dimethylamino)biphenyl (DavePhos).

The ligand may also be added in a catalytic amount. In some aspects, the ligand is provided in amounts ranging from 0.1 mol % to 10 mol % to the halogenated cluster boron reactant. In another embodiment, the ligand is added in an amount ranging from 0.5 mol % to about 5 mol % the halogenated cluster boron reactant. In various embodiments, the ligand is added to the reaction in an amount of about 0.5 mol %, about 1 mol %, about 1.5 mol %, about 2 mol %, about 2.5 mol %, about 3.0 mol %, about 3.5 mol %, about 4 mol %, about 4.5 mol %, about 5 mol %, about 5.5 mol %, about 6 mol %, about 6.5 mol %, about 7 mol %, about 7.5 mol %, about 8 mol %, about 8.5 mol %, about 9 mol %, about 9.5 mol % or about 10 mol % to the halogenated cluster boron compound.

A proton acceptor may facilitate the reaction. Preferably, the proton acceptor is a phosphate salt, for example, sodium phosphate, potassium phosphate, lithium phosphate, or calcium phosphate. Other acceptable bases include sodium t-butoxide, sodium hydride, caesium carbonate, potassium carbonate, caesium fluoride. In a preferred embodiment, the base is potassium phosphate. The base may be added in excess to the halogenated icosahedral reactant. In some embodiments, the mole to mole ratio of the halogenated cluster boron to the base can range from about 1:1.1 to about 1:20. In some embodiments, the mole to mole ratio of the cluster boron compound to the base is about 1:2, about 1:3, about 1:4, about 1:5, about 1:6, about 1:7, about 1:8, about 1:9, or about 1:10.

The reaction is generally conducted in a solvent. The solvent may be chosen without limitation from including alkane and substituted alkane solvents (including cycloalkanes) alcohol solvents, halogenated solvents, aromatic hydrocarbons, esters, ethers, ketones, and combinations thereof. Non-limiting examples of suitable organic solvents are acetonitrile, acetone, allyl alcohol, benzene, butyl acetate, chlorobenzene, chloroform, chloromethane, cyclohexane, cyclopentane, dichloromethane (DCM), dichloroethane, diethyl ether, dimethoxyethane (DME), dimethyl sulfoxide (DMSO), dioxane, ethanol, ethyl acetate, ethylene dichloride, ethylene bromide, formic acid, fluorobenzene, heptane, hexane, isobutylmethylketone, isopropanol, isopropyl acetate, N-methylpyrrolidone, methanol, methylene bromide, methylene chloride, methyl iodide, methylethylketone, methyltetrahydrofuran, pentyl acetate, propanol, n-propyl acetate, sulfolane, tetrahydrofuran (THF), tetrachloroethane, toluene, trichloroethane, water, xylene and combinations thereof. In a preferred embodiment the solvent is tetrahydrofuran (THF) and toluene.

The reaction is generally conducted at a temperature ranging from about 50° C. to about 150° C. In some embodiments, the reaction is conducted at about 60° C., about 65° C., about 70° C., about 75° C., about 80° C., about 85° C., about 90° C., about 95° C., about 100° C., about 105° C., about 110° C., about 115° C., or about 120° C.

The amount of time over which the reaction is conducted may also vary. In some embodiments, the reaction may be conducted over a period of 1 hour to about 24 hours. In various embodiments, the reaction may be conducted over a period of about a half hour, about 1 hour, about 1.5 hours, about 2 hours, about 2.5 hours, about 3 hours, about 3.5 hours, about 4 hours, about 4.5 hours, or about 5 hours.

In one embodiment, an iodine carborane may be reacted with an amino acetamide in the presences of a transition metal catalyst. FIG. 3 illustrates an exemplary synthetic scheme where 9-iodo-m-carborane is reacted with 2-diethylaminoacetamide in the presence of $K_3PO_4$, DavePhos ligand, and $Pd_2(dba)_3$ in refluxing THF.

The yield of the reaction can and will vary. In some embodiments, the yield may be at least about 80%. In still another embodiment, the yield of the compound of Formula (II) may be greater than about 85%, about 90% or about 95%. In still another embodiment, the yield may be about 95%. The compositions may be purified by methods known in the art including crystallization, chromatography, filtration and the like. The purified isolated yield may similarly be greater than about 85%, about 90% or about 95%

The compositions comprising Formula (II) and (III) may be synthesized from a hydroxylated cluster boron compound. Hydroxylation of the cluster boron compound may be achieved with a soft electrophile and a carbonate, or may be achieved by use of hydrogen peroxide, for example as described in U.S. Pat. No. 6,323,372. Hydroxylation and subsequent modifications may also be achieved as described in Russell N. Grimes, *Carboranes*, Elsevier Press (2011), which is hereby incorporated by reference.

(IV). Methods of Use

In another aspect of the present invention, the disclosure provides a method of treating a condition associated with sodium channel function in a subject, the method comprising administering to the subject a cluster boron substituted lidocaine or cluster boron substituted lidocaine derivative.

Lidocaine derivates, as used herein, are topical analgesics in the same class as lidocaine. Lidocaine derivatives include amino amide lidocaine derivatives, ester lidocaine derivatives, amino ester lidocaine derivatives, amino ether lidocaine derivatives, and amino keto lidocaine derivatives. Specific lidocaine derivatives include, but are not limited to benzocaine, bupivacaine, ropivacaine, cocaine, etidocaine, mepivacaine, pramoxine, prilocaine, procaine, chloroprocaine, proparacaine, mexiletine, and tetracaine. As is understood in the art, lidocaine and lidocaine derivatives generally have an aromatic functional group, which is generally a phenyl ring. In the compounds described herein, the aromatic moiety of the lidocaine analog is replaced by a cluster boron as described in section (I). Where the aromatic moiety of a lidocaine or lidocaine derivative has been replaced by a cluster boron moiety, the result is a cluster boron substituted lidocaine or an icosahedral substituted lidocaine derivative.

The compounds of the invention may be used in conditions associated with sodium channel function by blocking sodium channel function. Conditions associated with sodium channel function which may be treated with the compounds of the invention include, without limitation, acute, inflammatory, and neuropathic pain, abnormal cardiac rhythms, seizures, and depression. In exemplary embodiments, the compounds of the invention induce analgesia in a subject.

Many types of sodium channels are known and the compositions may be used to target particular sodium channels. The compounds may exhibit selectivity for one or more sodium channels chosen from $Na_v1.1$, $Na_v1.2$, $Na_v1.3$, $Na_v1.4$, $Na_v1.5$, $Na_v1.6$, $Na_v1.7$, $Na_v1.8$ and $Na_v1.9$. In some embodiments, the compounds are selective for sensory nerves, and in other embodiments, the compounds are selective to motor nerves.

The compounds may be administered to the subject by a variety of routes. For example, a compound comprising Formula (I), (II), or (III) may be administered orally (via a solid or liquid dosage form), parenterally (i.e., subcutaneously, intradermally, intravenously, intramuscularly, intracranially, or intraperitoneally), or topically (i.e., transdermally or transmucosally).

Suitable subjects include, without limit, humans, as well as companion animals such as cats, dogs, rodents, and horses; research animals such as rabbits, sheep, pigs, dogs, primates, mice, rats and other rodents; agricultural animals such as cows, cattle, pigs, goats, sheep, horses, deer, chickens and other fowl; zoo animals; and primates such as chimpanzees, monkeys, and gorillas. In a preferred embodiment, the subject may be a human.

The compounds may be administered in saline or with a pharmaceutically acceptable excipient as described in section (II). The amount of the compound which is administered to the subject may depend on the subject and the route of administration and can be determined by a person of ordinary skill in the art.

In some aspects, the cluster boron lidocaine analogs provide for a longer duration of therapeutic action. Without being bound to any theory it is hypothesized that the greater hydrophobicity of the cluster boron compounds in comparison to an aromatic functionality such as phenyl, the longer durations of therapeutic activity. In particular, longer durations of analgesia have been shown.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "epoxy" or "epoxide" as used herein means a cyclic ether. The ring structure generally comprises from 2 to 5 carbon atoms in the ring.

The terms "halide" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thiol.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

EXAMPLES

General Procedures

All coupling reactions were carried out under argon using Schlenk techniques. Toluene was freshly distilled from $CaH_2$ prior to use and tetrahydrofuran (THF) was dried by passage through solvent purification system VAC to provide water content of less than 25 ppm as was determined by coulometric KF titrator Mettler Toledo. All other solvents were used as purchased from commercial sources. 2-Dicyclohexylphosphino-2-(N,N-dimethylamino)biphenyl (DavePhos), diethylamine, 2-bromoacetamide and tris(dibenzylideneacetone) dipalladium were used as purchased (Sigma-Aldrich, St.-Louis, Mo.). The 2-diethylaminoacetamide was synthesized following in-house developed procedure. All iodo-carboranes were azeotropically dried with benzene to remove any trace of water. Tribasic potassium phosphate was ground to a fine powder and then dried thoroughly by heating under vacuum at 105° C. All solids were stored in an argon-filled glove box. Silica gel was used as purchased (63-200 μm, Sorbent Technologies, Inc.). Analytical thin-layer chromatography (TLC) for carborane identification was performed by using pre-coated silica-gel XHL plates (Sorbent Technologies, Inc.) and visualized by dipping into an acidified (hydrochloric acid) solution of $PdCl_2$ followed by heating. $^{11}B$ NMR spectra were obtained using BrukerAvance 400 and Avance 500 spectrometers and externally referenced to $BF_3 \cdot Et_2O$ and the peaks upfield of the reference were designated as negative. $^1H$ NMR and $^{13}C$ NMR spectra were acquired on BrukerAvance 400 and Avance 500 spectrometers. Chemical shifts are given in ppm relative to residual solvent signals ($CDCl_3$, δ=7.24 ppm for $^1H$ NMR and 77.0 ppm for $^{13}C$ NMR). $^{19}F$ NMR spectra were acquired on BrukerAvance 400 and chemical shifts are given relative to the external $BF_3$-$Et_2O$ reference (δ=−153.0 ppm). Mass spectra were obtained on an ABI QSTAR and Mariner Biospectrometry Workstation by PerSeptive Biosystems. Melting points were obtained using automated melting point system OptiMelt (Stanford research system). Measurements were conducted in open-end Kimble Chase capillary tubes from borosilicate glass (L=90 mm). The melting point range is defined as the interval between the onset and clear points using 0.5° C./min ramp rate.

Example 1

Synthesis of 2-Diethylaminoacetamide 2 g of 2-bromoacetamide (0.015 mol) were slowly added to diethylamine (40 mL, 0.387 mol) and the reaction mixture was heated to reflux for 20 h. After cooling to room temperature, the reaction mixture was filtered and precipitate discarded. The filtrate was concentrated under vacuum to result in slightly yellow solid. This solid was dissolved in chloroform (10 mL) and washed with aqueous saturated solution of $Na_2CO_3$ (3×10 mL). Combined organic phases were dried over $Na_2SO_4$. The filtrate was concentrated under vacuum to result in 1.49 g (79% yield) of light yellow solid, which was azeotropically dried with benzene prior to use in the following reactions. $^1H$ NMR (500 MHz, $CDCl_3$, J=Hz): δ 6.19 (2H, s, br, $NH_2$), 3.01 (2H, s, $CH_2$), 2.56 (4H, q, J 7.2, $NEt_2$), 1.04 (6H, t, J 7.3, $NEt_2$). $^{13}C$ NMR (125.8 MHz, CDCl3): δ 175.6 (C=O), 57.4 ($CH_2$), 48.6, 12.3 ($NEt_2$). HRMS (ESIMS) m/z for $C_6H_{15}N_2O$ $[M+H]^+$ calcd 131.1184, found 131.0907.

Example 2

Synthesis of 3-Diethylaminoacetamido-1,2-closo-carborane

Into an argon-filled glove box was brought a dry 25 mL Schlenk flask, where was added 300 mg (1.10 mmol) of the 3-iodo-o-carborane, 432 mg (3.32 mmol) of 2-diethylaminoacetamide, 1.13 g (5.35 mmol) of $K_3PO_4$, 21 mg (0.05 mmol) of DavePhos ligand, 24 mg (0.03 mmol) $Pd_2(dba)_3$ and a Teflon-coated magnetic stir bar. The flask was then capped with a stopper and 4 mL of dry toluene was added by syringe at the Schlenk line. The reaction mixture was refluxed for 2 h, after which it was filtered and the filtrate evaporated to leave yellow oily residue. The residue was then dissolved in dichloromethane and added directly to the top of a silica column. The product was eluted beginning with 0:100 methanol:dichloromethane mixture and then stepwise increasing the concentration of methanol (i.e., mixture of 5% diethylamine in methanol). Once the compound was isolated from a column, the volatiles were removed by rotary evaporator to provide the slightly yellow solid in 62% yield (180 mg). Further purification to obtain white crystalline material was accomplished by passing through active carbon column (130 mg, 45% yield). $^1H$ NMR (500 MHz, $CDCl_3$, J=Hz): δ 8.04 (1H, S, CONH), 4.52 (2H, s, $C_{carborane}$—H), 3.04 (2H, s, $CH_2$), 2.66 (4H, q, J 6.7, $NEt_2$), 1.12 (6H, t, J 7.5, $NEt_2$), 3.0-1.3 (m, 9H, BH). $^{13}C$ NMR (125.8 MHz, CDCl3): δ 176.7 (C=O), 57.7, 54.6 ($CH_2+C_{carborane}$), 48.9, 12.2 ($NEt_2$). $^{11}B$ NMR (160.5 MHz, CDCl3), J=Hz): δ −4.8 (2B, d, J 148), −6.7 (1B, s), −11.1 (1B, d, J 151), −13.0 (2B, d, J 167), −15.1 (4B, d, J 141). HRMS (ESIMS) m/z for $C_8H_{24}N_2OB_{10}$ [M-H] calcd 271.2818, found 271.2061.

Example 3

Synthesis of 9-Diethylaminoacetamido-1,7-closo-carborane

Into an argon-filled glove box was brought a dry 25 mL Schlenk flask, where was added 500 mg (1.85 mmol) of the 9-iodo-m-carborane, 722 mg (5.54 mmol) of 2-diethylaminoacetamide, 1.96 g (9.23 mmol) of $K_3PO_4$, 44 mg (0.11 mmol) of DavePhos ligand, 42 mg (0.05 mmol) $Pd_2(dba)_3$ and a Teflon-coated magnetic stir bar. The flask was then capped with a stopper and 20 mL of dry THF was added by syringe at the Schlenk line. The reaction mixture was heated to reflux for 3 days, after which it was filtered and the filtrate evaporated to leave yellow crude solid. The residue was then dissolved in methanol and evaporated with about 10 mL of $SiO_2$ (63-200 μm) and then twice coevaporated with a small amount of dichloromethane. The solid was added directly to the top of a silica column and eluted beginning with 0:100 methanol:dichloromethane mixture and then stepwise increasing the concentration of methanol (i.e., mixture of 5% diethylamine in methanol). Once the compound was isolated from the column, the volatiles were removed by rotary evaporator to provide the yellowish solid. Washing solid with diethyl ether resulted in white crystalline powder in 86% yield (432 mg). Mp 127.9-129.2° C. $^1$H NMR (400 MHz, DMSO-d$_6$, J=Hz): δ 7.05 (1H, s, CONH), 3.82 (2H, s, C$_{carborane}$—H), 2.80 (2H, s, CH$_2$), 2.42 (4H, q, J 7.1, NEt$_2$), 0.88 (6H, t, J 7.2, NEt$_2$), 3.2-1.1 (m, 9H, BH). $^{13}$C NMR (100.6 MHz, DMSO-d$_6$): δ 173.6 (C=O), 58.0, 52.9 (CH$_2$+C$_{carborane}$), 48.1, 12.2 (NEt$_2$). $^{11}$B NMR (128.4 MHz, DMSO-d$_6$, J=Hz): δ −0.5 (1B, s), −7.7 (2B, d, J 139), −11.6 (1B, d, J 146), −14.2 (2B, d, J 184), −15.8 (2B, d, J 167), −18.8 (1B, d, J 173), −22.2 (1B, d, J 148). HRMS (ESIMS) m/z for C$_8$H$_{26}$N$_2$OB$_{10}$ [M+2H] calcd 274.3053, found 274.3141.

Example 4

Synthesis of 2-Diethylaminoacetamido-1,12-closo-carborane

Into an argon-filled glove box was brought a dry 25 mL Schlenk flask, where was added 1.0 g (3.69 mmol) of the 2-iodo-p-carborane, 630 mg (4.85 mmol) of 2-diethylaminoacetamide, 3.91 g (18.45 mmol) of K$_3$PO$_4$, 71 mg (0.18 mmol) of DavePhos ligand, 169 mg (0.18 mmol) of Pd$_2$(dba)$_3$ and a Teflon-coated magnetic stir bar. The flask was then capped with a stopper and 20 mL of dry THF was added by syringe at the Schlenk line. The reaction mixture was heated to reflux for 2 days, after which it was filtered and the red color filtrate evaporated with about 5 mL of SiO$_2$ (63-200 μm) and then twice coevaporated with a small amount of dichloromethane. Towards the end, the concentration of 5% diethylamine in methanol mixture was stepwise increased for complete isolation. The solid was added directly to the top of a silica column and eluted with dichloromethane. Once the compound was isolated from the column, the volatiles were removed by a rotary evaporator to provide the slightly yellow solid in 93% yield (940 mg). Product, in form of hydrochloride salt, was further purified by recrystallization from methanol/ether mixture. $^1$H NMR (400 MHz, CDCl$_3$, J=Hz): δ 7.54 (1H, s, br, CONH), 3.71 (1 H, s, C$_{carborane}$—H), 2.93 (2H, s, CH$_2$), 2.68 (1H, s, C$_{carborane}$—F), 2.55 (4H, q, J7.2, NEt$_2$), 1.03 (6H, t, J 7.2, NEt$_2$), 3.1-1.1 (m, 9H, BH). $^{13}$C NMR (125.8 MHz, CDCl$_3$): δ 175.9 (C=O), 64.7, 60.5 (C$_{carborane}$), 58.4 (CH$_2$), 49.0, 12.5 (NEt$_2$). $^{11}$B NMR (128.4 MHz, CDCl$_3$, J=Hz): δ −5.1 (1B, 5), −13.9 (2B, d, J 190), −15.5 (4B, d, J 161), −16.5 (2B, d, J 139), −19.9 (1 B, d, J 162). HRMS (ESIMS) m/z for C$_8$H$_{26}$N$_2$OB$_{10}$ [M+2H] calcd 274.3053, found 274.3561.

Example 5

General Procedure for Preparing Hydrochloride Salts of Compounds

The appropriate compound (Examples 2-4) was dissolved in diethyl ether and the HCl gas was bubbled through a stirred solution for 20 to 40 min at a medium rate. White precipitate, which was formed during this process, was filtered and recrystallized from the methanol/ether mixture to result in shiny white crystals of the respective hydrochloride salt.

Example 6

X-Ray Diffraction Studies

The X-ray quality crystals of compound in Example 3 (m-lidocaine carborane) were obtained upon slow evaporation of the dichloromethane/hexane mixture. Data collection for the studied crystals was carried out at −100° C. on a Bruker SMART 1000 CCD area detector system using the w scan technique with Mo Kα radiation (λ=0.71073 Å) from a graphite monochromator. Data reduction and integration were performed with the software package SAINT (Bruker, SAINT v 7.68A; BrukerAXS Inc.: Madison, Wis., 2009). Data were corrected for absorption using SADABS (Sheldrick, G. M. SADABS 2008/1; Gottingen, 2008). The crystal structure was solved with the direct methods program SHELXS-97 and was refined by full matrix least squares techniques with the SHELXTL (Sheldrick, G. M. SHELXTL, version 6.14; Bruker AXS, Inc.: Madison, Wis., 2001.) suite of programs. The colorless block of 9-diethylaminoacetamido-1,7-closo-carborane (0.20×0.14×0.08 mm) was analyzed at 173(2) K and found to be monoclinic, space group P2$_1$/c, a=7.3524(9) Å, b=10.2414(12) Å, c=21.641(3) Å, β=96.762(2)°, V=1618.2(3) Å$^3$, Z=4. A total of 18341 reflections were collected in the range 1.90<θ>27.32°. All non-hydrogen atoms were refined anisotropically. The refinement of hydrogen atoms was mixed. The final refinement cycle was based on 3642 reflections and 200 parameters. The final R1 value was 0.0505 (wR2=0.1277) for 2535 reflections [I>2σ (I)]. The maximum and minimum peaks in the final difference Fourier map corresponded to 0.273 and −0.212 e/Å3, with a goodness-of-fit value of 1.019.

Example 7

Electrophysiology Experiments

In vitro electrophysiology experiments in cells show that lidocaine and the o-, m-, and p-carborane derivatives of lidocaine block voltage gated sodium channels in a reversible manner. Na$_v$1.2 voltage gated sodium channels were expressed in *Xenopus oocytes* and standard two electrode voltage clamp techniques were used to measure ionic currents through the channels after depolarizations from a holding potential of −50 mV. The test drugs, all at a concentration of 0.3 mM, were added to the superfusate for two minutes as indicated by the black bars and then washed out. Control experiments showed that addition of a drug-free solution had no effect. Data are expressed as means±standard error of the mean and n equals the number of cells used in FIG. 4(a)-(d).

Example 8

In vivo Experiments

In vivo experiments in mice show that lidocaine and o- and p-carborane lidocaine provide analgesia in hot plate experiments. The m-carborane lidocaine did not provide analgesia similar to control experiments with saline injections which were not analgesic. The test drugs, all at a volume of 50 microliters and a concentration of 10 mM, were injected into a hind limb near the sciatic nerve. The time it takes for the animals to withdraw the foot of the injected limb from touching a 55° C. hot plate is measured in seconds. This time is termed the paw withdrawal latency and is measured over about a 30 min time period. Data are expressed as means±standard error of the mean and n equals the number of animals used in FIG. 5(a)-(d).

Example 9

Motor Block Accompanying Sensory Block

Figure 6:
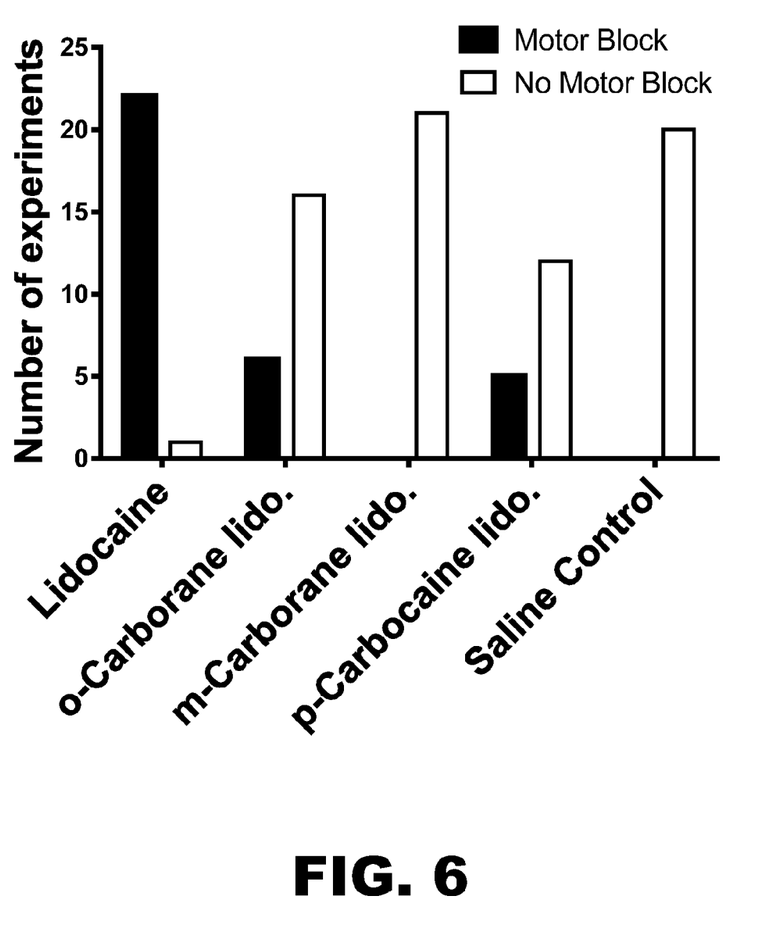
FIG. 6 shows selectivity of lidocaine, o-carborane lidocaine, m-carborane lidocaine, p-carborane lidocaine against control. o-carborane lidocaine and p-carborane lidocaine provided selective block of sensory nerves over motor nerves compared to lidocaine.

Motor deficit testing of the mice after injection showed that the o- and p-carborane lidocaine derivatives selectively blocked sensory nerves over motor nerves. Motor function was tested by observing the ability of the mice to walk hanging upside down from a screen, termed the inverted screen test. FIG. 6 shows the number of experiments in which there was motor block and the number of experiments in which there was no motor block for each compound. Whereas nearly all the lidocaine experiments showed motor block, fewer o-and p-carborane lidocaine experiments showed motor block. The m-carborane lidocaine and the saline experiments showed neither motor nor sensory block in the mice.

What is claimed is:

1. A method of treating a condition associated with sodium channel function in a subject in need of treatment, the method comprising administering to the subject a carborane substituted lidocaine or carborane substituted lidocaine derivative comprising Formulae (I)(b)-(g), (II), or (Ill):

Formula (I)(b)

Formula (I)(c)

Formula (I)(d)

Formula (I)(e)

Formula (I)(f)

Formula (I)(g)

Formula (II)

Formula (III)

wherein
B is a carborane;
R$^1$ represents hydrocarbyl or substituted hydrocarbyl;
R$^2$ and R$^3$ are independently chosen from hydrocarbyl and substituted hydrocarbyl;
and R$^1$, R$^2$ and R$^3$ may form one or more rings.

2. The method of claim 1, wherein the carborane is a closo or nido carborane.

3. The method of claim 1, wherein the lidocaine derivative comprises Formula (II):

Formula (I)

4. The method of claim 3, wherein R$^1$ is chosen from —CH$_2$—, —CH(CH$_3$)—, —C(CH$_3$)$_2$—, —CH$_2$CH$_2$—, CH$_2$CH(CH$_3$)—, and —CH(CH$_2$CH$_3$)—.

5. The method of claim 3, wherein R$^2$ and R$^3$ are independently chosen from methyl, ethyl, propyl, and butyl.

6. The method of claim 1, wherein the lidocaine formula comprises Formula (I)(b)-(g).

7. The method of claim 1, wherein the carborane is a polyhedral carborane with two carbon atoms and ten boron atoms in an ortho, meta, or para isomer, comprising unsubstituted or substituted carbon atoms and unsubstituted or substituted boron atoms.

8. The method of claim 1, wherein the lidocaine formula comprises one of Formulae (I)(b)-(g), and wherein the carborane is a polyhedral carborane with two carbon atoms and ten boron atoms in an ortho, meta, or para isomer, comprising unsubstituted or substituted carbon atoms and unsubstituted or substituted boron atoms.

9. The method of claim 1, wherein the lidocaine derivative comprises Formula (III):

Formula (III)

10. The method of claim 9, wherein R$^1$ is chosen from —CH$_2$—, —CH(CH$_3$)—, —C(CH$_3$)$_2$—, —CH$_2$CH$_2$—, CH$_2$CH(CH$_3$)—, and —CH(CH$_2$CH$_3$)—.

11. The method of claim 9, wherein R$^2$ and R$^3$ are independently chosen from methyl, ethyl, propyl, and butyl.

12. The method of claim 1, wherein the condition associated with sodium channel function is selected from the group consisting of acute pain, inflammatory pain, neuropathic pain, abnormal cardiac rhythms, seizures, and depression.

* * * * *